(12) United States Patent
Mikhno et al.

(10) Patent No.: US 12,690,818 B2
(45) Date of Patent: Jul. 28, 2026

(54) EVENT-ORIENTED PREDICTIONS OF GLYCEMIC RESPONSES

(71) Applicant: Medtronic MiniMed, Inc., Northridge, CA (US)

(72) Inventors: Arthur Mikhno, Princeton, NJ (US); Yuxiang Zhong, Arcadia, CA (US); Dae Y. Kang, Los Angeles, CA (US); Michael P. Stone, Long Beach, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 972 days.

(21) Appl. No.: 17/852,878

(22) Filed: Jun. 29, 2022

(65) Prior Publication Data

US 2023/0000447 A1     Jan. 5, 2023

Related U.S. Application Data

(60) Provisional application No. 63/304,090, filed on Jan. 28, 2022, provisional application No. 63/216,865, filed on Jun. 30, 2021.

(51) Int. Cl.
*G16H 20/17*         (2018.01)
*A61B 5/00*          (2006.01)
(Continued)

(52) U.S. Cl.
CPC ........ *A61B 5/7275* (2013.01); *A61B 5/14532* (2013.01); *A61B 5/7282* (2013.01); *A61P 3/08* (2018.01); *G16H 20/10* (2018.01)

(58) Field of Classification Search
None
See application file for complete search history.

(56) References Cited

U.S. PATENT DOCUMENTS

2010/0160758 A1* 6/2010 Okada ................. A61B 5/7242
                                                        600/365
2010/0280329 A1* 11/2010 Randlov ............... G16H 50/50
                                                        600/300
(Continued)

FOREIGN PATENT DOCUMENTS

WO         0205702 A2    1/2002
WO      2011050337 A1    4/2011
WO      2020068191 A1    4/2020

OTHER PUBLICATIONS

International Search Report and Written Opinion dated Oct. 4, 2022, in PCT Application No. PCT/US2022/035651.
(Continued)

*Primary Examiner* — Tse W Chen
*Assistant Examiner* — Martin Nathan Ortega
(74) *Attorney, Agent, or Firm* — Weaver Austin Villeneuve & Sampson LLP

(57)         ABSTRACT

Disclosed herein are techniques related to event-oriented predictions of glycemic responses. In some embodiments, the techniques may involve accessing a prediction model that correlates a person's glycemic responses to events and the person's physiological parameters during the events. The techniques may also involve obtaining a glucose level measurement of the person during an event. Additionally, the techniques may involve determining, based on the glucose level measurement, a physiological parameter of the person during the event. Furthermore, the techniques may involve predicting the person's glycemic response to the event based on applying the prediction model to the physiological parameter.

20 Claims, 11 Drawing Sheets

(51) Int. Cl.
  A61B 5/145 (2006.01)
  A61P 3/08 (2006.01)
  G16H 20/10 (2018.01)

(56)                    References Cited

U.S. PATENT DOCUMENTS

| 2016/0296132 A1* | 10/2016 | Bojovic | ................. | G16H 40/63 |
| 2017/0007148 A1* | 1/2017 | Kaditz | ................... | A61B 5/055 |
| 2020/0101221 A1* | 4/2020 | Lintereur | ............. | A61B 5/7275 |
| 2022/0062544 A1* | 3/2022 | El Fathi | ................. | G16H 50/50 |
| 2022/0203029 A1* | 6/2022 | Breton | ................. | A61B 5/4836 |

OTHER PUBLICATIONS

International Preliminary Report on Patentability and Written Opinion dated Jan. 11, 2024 in PCT Application No. PCT/US2022/035651.

* cited by examiner

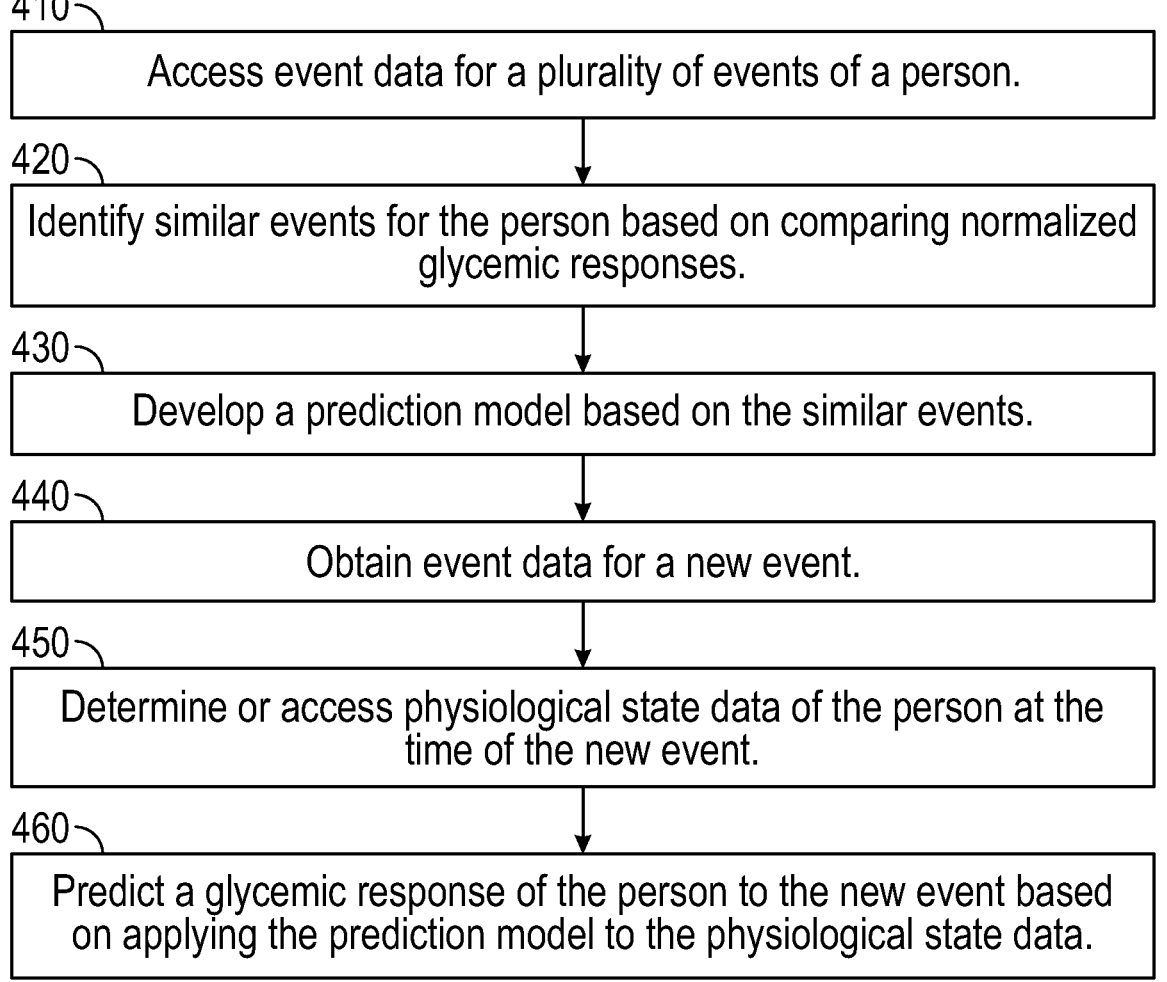

410 — Access event data for a plurality of events of a person.

420 — Identify similar events for the person based on comparing normalized glycemic responses.

430 — Develop a prediction model based on the similar events.

440 — Obtain event data for a new event.

450 — Determine or access physiological state data of the person at the time of the new event.

460 — Predict a glycemic response of the person to the new event based on applying the prediction model to the physiological state data.

FIG. 4

Event with Borrowed Physiological State

| | 1 | 2 | 3 | · · · | m |
|---|---|---|---|---|---|
| 1 | | O | O | O | X |
| 2 | O | | O | X | O |
| 3 | O | X | | O | O |
| · · · | O | X | O | | O |
| m | O | O | O | X | |

*Event with Derived Physiological State*

EVENT-ORIENTED PREDICTIONS OF GLYCEMIC RESPONSES

CROSS-REFERENCE TO RELATED APPLICATIONS

The present application claims the benefit of and priority to U.S. Provisional Application No. 63/216,865, filed Jun. 30, 2021, and to U.S. Provisional Application No. 63/304, 090, filed Jan. 28, 2022. The entire contents of each of the foregoing applications are hereby incorporated by reference herein.

TECHNICAL FIELD

The present disclosure relates generally to the medical arts and more particularly to event-oriented predictions of glycemic responses.

BACKGROUND

A person may use insulin therapy to manage type I or type II diabetes. Insulin therapy may include use of insulin infusion systems for delivering or dispensing insulin. An insulin infusion system may include an infusion device which typically includes a small motor and drive train components configured to deliver insulin from a reservoir into the body of a person, e.g., via a percutaneous needle or a cannula placed in the subcutaneous tissue. Insulin infusion systems may facilitate management of diabetes for some persons.

SUMMARY

Disclosed herein are techniques related to event-oriented predictions of glycemic responses. The techniques may be practiced in a variety of ways, such as using a processor-implemented method; a system comprising one or more processors and one or more processor-readable media; and/or one or more (non-transitory) processor-readable media.

In accordance with aspects of the present disclosure, the techniques may involve accessing a prediction model that correlates a person's glycemic responses to events and the person's physiological parameters during the events. The techniques may also involve obtaining a glucose level measurement of the person during an event. Additionally, the techniques may involve determining, based on the glucose level measurement, a physiological parameter of the person during the event. Furthermore, the techniques may involve predicting the person's glycemic response to the event based on applying the prediction model to the physiological parameter.

BRIEF DESCRIPTION OF THE DRAWINGS

The above and other aspects and features of the disclosure will become more apparent in view of the following detailed description when taken in conjunction with the accompanying drawings wherein like reference numerals identify like elements.

FIG. 4 is a block diagram of exemplary techniques for glycemic response prediction, in accordance with aspects of the present disclosure;

FIG. 8 is a diagram of a table showing exemplary similarity determinations for events, in accordance with aspects of the present disclosure;

DETAILED DESCRIPTION

Figure 1:
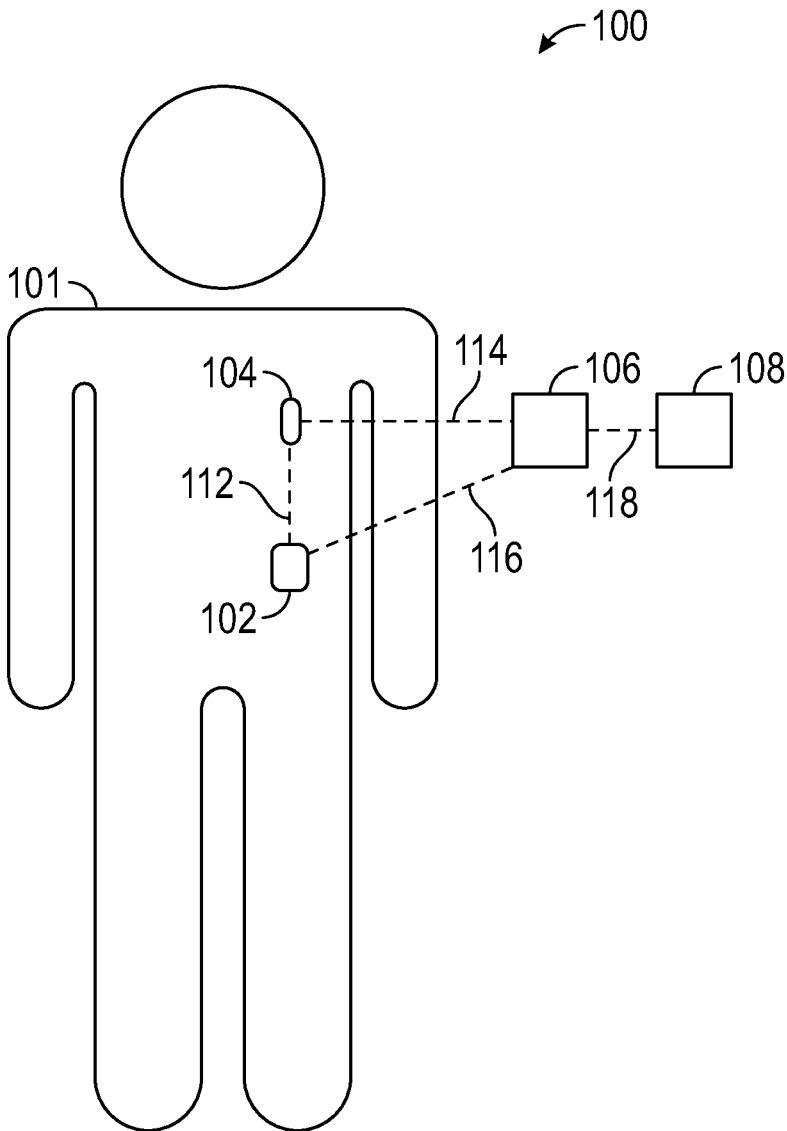
FIG. 1 is a diagram of an exemplary therapy delivery system, in accordance with aspects of the present disclosure.

In diabetes therapy, considerable effort has been expended to develop closed-loop insulin delivery systems. In particular, there is interest in developing a closed-loop system capable of predicting glycemic responses to various events. As used herein, an event may refer to a meal event, an exercise event, a sleep event, an illness event, or any other occurrence that can affect glucose levels. The term "glycemic response" refers to a change in glucose levels resulting from an event and can be represented as a series of glucose levels over time.

Some approaches for predicting glycemic response involve modeling glucose dynamics based on glucose levels measured prior to an event. For example, a glycemic response to a meal event can be predicted based on extrapolation from glucose levels measured prior to the meal. However, predictions made in such a manner tend to lose accuracy as the event progresses. This is at least partly due to variability among events. For example, a glycemic response to a lunch meal may differ from a glycemic response to a dinner meal due to differences in meal characteristics (e.g., carbohydrate intake may be different at lunch versus dinner) and physiological context (e.g., a person's metabolism may be different at lunch versus dinner). Thus, modeling the same glucose dynamics for all events can result in glycemic response predictions that become increasingly inaccurate over time.

Accordingly, disclosed herein are event-oriented approaches for predicting glycemic responses. Such approaches enable glycemic response predictions that account for variability among events. For example, such approaches may take into consideration event characteristics (e.g., carbohydrate content of a meal) and physiological context (e.g., a person's metabolic rates at the time of the meal) when predicting glycemic responses. Thus, the techniques disclosed herein provide a robust approach that enables increased accuracy of glycemic response predictions even several hours after the start of an event.

The present disclosure is described primarily with respect to insulin delivery systems. Aspects and embodiments of the present disclosure can be practiced with one or more types of insulin (e.g., fast-acting insulin, intermediate-acting insulin, and/or slow-acting insulin). Unless indicated by the context, terms such as "dose," "insulin," "basal," and "bolus" may not denote a particular type of insulin. For example, fast-acting insulin may be used for both basal dosages and bolus dosages. As used herein, the term "basal" refers to and includes insulin that is delivered in an amount and at a frequency that is intended to correspond to a healthy body's release of insulin between meals and during sleep. The term "bolus" refers to and includes insulin that is delivered in an amount and at a timing that is intended to correspond to a healthy body's release of insulin for counteracting a high glucose level, such as that caused by consumption of a meal. A meal may include any type or amount of food or beverage consumption, including breakfast, lunch, dinner, snacks, and beverages, among others.

Although the present disclosure may be described primarily with respect to insulin delivery systems, the scope of the present disclosure is not limited to insulin delivery systems. Rather, the present disclosure applies to and can be implemented for other therapy systems as well. It is intended that any aspects, embodiment, and description relating to insulin delivery systems shall be applicable to other types of therapy delivery systems as well.

Although the disclosure is not limited in this regard, discussions utilizing terms such as, for example, "processing," "computing," "calculating," "determining," "establishing," "analyzing," "checking," or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other non-transitory information storage media that may store instructions to perform operations and/or processes. As used herein, "exemplary" does not necessarily mean "preferred" and may simply refer to an example unless the context clearly indicates otherwise. Although the disclosure is not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term "set" when used herein may include one or more items. Unless explicitly stated, the methods described herein are not constrained to a particular order or sequence. Additionally, some of the described methods or elements thereof can occur or be performed simultaneously or concurrently.

Referring to FIG. 1, there is shown a diagram of an exemplary therapy delivery system 100 for a person 101. System 100 may be an insulin delivery system. The illustrated therapy delivery system 100 includes a delivery device 102, a monitoring device 104, a computing device 106, and an optional remote or cloud computing system 108. The delivery device 102, the monitoring device 104, and the computing device 106 may be embodied in various ways, including being disposed in one or more device housings. For example, in various embodiments, all of the devices 102-106 may be disposed in a single device housing. In various embodiments, each of the devices 102-106 may be disposed in a separate device housing. In various embodiments, two or more of the devices 102-106 may be disposed in the same device housing, and/or a single device 102, 104, or 106 may have two or more parts that are disposed in two or more housings. Such embodiments, and combinations thereof, are contemplated to be within the scope of the present disclosure.

FIG. 1 also illustrates communications links 112-118. The communications links 112-118 may each be a wired connection and/or a wireless connection. In the case where two devices are located in the same device housing, the communication link may include, for example, wires, cables, and/or communication buses on a printed circuit board, among other things. In the case where two devices are separated from each other in different device housings, the communication links may be wired and/or wireless connections. Wired connections may include, without limitation, an Ethernet connection, a USB connection, and/or another type of physical connection. Wireless connections may include, without limitation, a cellular connection, a Wi-Fi connection, a Bluetooth® connection, a mesh network connection, and/or another type of connection using a wireless communication protocol. Various embodiments of the communication links 112-118 may use direct connections, such as Bluetooth® connections, and/or may use connections that route through one or more networks or network devices (not shown), such as an Ethernet network, a Wi-Fi network, a cellular network, a satellite network, an intranet, an extranet, the Internet, and/or the Internet backbone, among other types of networks. Various combinations of wired and/or wireless connections may be used for the communication links 112-118.

Aspects of the insulin delivery system 100 are described below. Further aspects and details may be described in U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893. The entire contents of each of the foregoing United States Patents are hereby incorporated by reference herein.

The delivery device 102 is configured to deliver a therapeutic substance (e.g., insulin) to a person 101. The delivery device 102 may be secured to the person 101 (e.g., to the body or clothing of the person 101) or may be implanted on or in the body of the person 101. In various embodiments, the delivery device 102 may include a reservoir, an actuator, a delivery mechanism, and a cannula (not shown). The reservoir may be configured to store an amount of the therapeutic substance. In various embodiments, the reservoir may be refillable or replaceable. The actuator may be configured to drive the delivery mechanism. In some examples, the actuator may include a motor, such as an electric motor. The delivery mechanism may be configured to move the therapeutic substance from the reservoir through the cannula. In some examples, the delivery mechanism may include a pump and/or a plunger. The cannula may facilitate a fluidic connection between the reservoir and the body of the person 101. The cannula and/or a needle may facilitate delivery of the therapeutic substance to a tissue layer, vein, or body cavity of the person 101. During operation, the actuator, in response to a signal (e.g., a command signal), may drive the delivery mechanism, thereby causing the therapeutic substance to move from the reservoir, through the cannula, and into the body of the person 101.

The components of the delivery device 102 described above are exemplary. The delivery device 102 may include other components, such as, without limitation, a power supply, a communication transceiver, computing resources, and/or user interfaces, among other things. Persons skilled in the art will recognize various implementations of the delivery device 102 and the components of such implementations. All such implementations and components are contemplated to be within the scope of the present disclosure.

With continuing reference to FIG. 1, the monitoring device 104 is configured to detect a physiological condition (e.g., a glucose concentration level) of the person 101 and may also be configured to detect other things. The monitoring device 104 may be secured to the body of the person 101 (e.g., to the skin of person 101 via an adhesive) and/or may be at least partially implanted into the body of the person 101. Depending on the particular location or configuration, the monitoring device 104 may be in contact with biological matter (e.g., interstitial fluid and/or blood) of the person 101.

The monitoring device 104 includes one or more sensors (not shown), such as, without limitation, electrochemical sensors, electrical sensors, and/or optical sensors. As persons skilled in the art will understand, an electrochemical sensor may be configured to respond to the interaction or binding of a biological marker to a substrate by generating an electrical signal based on a potential, conductance, and/or impedance of the substrate. The substrate may include a material selected to interact with a particular biomarker, such as glucose. The potential, conductance, and/or impedance may be proportional to a concentration of the particular biomarker. In the case of electrical sensors, and as persons skilled in the art will understand, an electrical sensor may be configured to respond to an electrical biosignal by generating an electrical signal based on an amplitude, frequency, and/or phase of the electrical biosignal. The electrical biosignal may include a change in electric current produced by the sum of an electrical potential difference across a tissue, such as the nervous system, of the person 101. In various embodiments, the electrical biosignal may include portions of a potential change produced by the heart of the person 101 over time, e.g., recorded as an electrocardiogram, that are indicative of a glucose level of the person 101. In the case of optical sensors, as persons skilled in the art will understand, an optical sensor may be configured to respond to the interaction or binding of a biological marker to a substrate by generating an electrical signal based on change in luminance of the substrate. For example, the substrate may include a material selected to fluoresce in response to contact with a selected biomarker, such as glucose. The fluorescence may be proportional to a concentration of the selected biomarker.

In various embodiments, the monitoring device 104 may include other types of sensors that may be worn, carried, or coupled to the person 101 to measure activity of the person 101 that may influence the glucose levels or glycemic response of the person 101. As an example, the sensors may include an acceleration sensor configured to detect an acceleration of the person 101 or a portion of the person 101, such as the person's hands or feet. The acceleration (or lack thereof) may be indicative of exercise, sleep, or food/beverage consumption activity of the person 101, which may influence the glycemic response of the person 101. In various embodiments, the sensors may include heart rate and/or body temperature, which may indicate an amount of physical exertion experienced by the person 101. In various embodiments, the sensors may include a GPS receiver which detects GPS signals to determine a location of the person 101.

The sensors described above are exemplary. Other sensors or types of sensors for monitoring physiological condition, activity, and/or location, among other things, will be recognized by persons skilled in the art and are contemplated to be within the scope of the present disclosure. For any sensor, the signal provided by a sensor shall be referred to as a "sensor signal."

The monitoring device 104 may include components and/or circuitry configured to preprocess sensor signals. Preprocessing may include, without limitation, amplification, filtering, attenuation, scaling, isolation, normalization, transformation, sampling, and/or analog-to-digital conversion, among other things. Persons skilled in the art will recognize various implementations for such preprocessing, including, without limitation, implementations using processors, controllers, ASICS, integrated circuits, hardware, firmware, programmable logic devices, and/or machine-executable instructions, among others. The types of preprocessing and their implementations are exemplary. Other types of preprocessing and implementations are contemplated to be within the scope of the present disclosure. In various embodiments, the monitoring device 104 may not perform preprocessing.

As used herein, the term "sensed data" shall mean and include the information represented by a sensor signal or by a preprocessed sensor signal. In various embodiments, sensed data may include glucose levels in a person 101, acceleration of a part of the person 101, heart rate of the person 101, temperature of the person 101, and/or geolocation (e.g., GPS location) of the person 101, among other things. The monitoring device 104 may communicate sensed data to the delivery device 102 via communication link 112 and/or to the computing device 106 via communication link 114. Use of sensed data by the delivery device 102 and/or by the computing device 106 will be described later herein.

The computing device 106 provides processing capabilities and may be implemented in various ways. In various embodiments, the computing device 106 may be a consumer device, such as a smartphone, a computerized wearable device (e.g., a smartwatch), a tablet computer, a laptop computer, or a desktop computer, among others, or may be a special purpose device (e.g., a portable control device) provided by, for example, the manufacturer of the delivery device 102. In various embodiments, the computing device 106 may be "processing circuitry" (defined below) that is integrated with another device, such as the delivery device 102. In various embodiments, the computing device 106 may be secured to the person 101 (e.g., to the body or clothing of person 101), may be at least partially implanted into the body of person 101, and/or may be held by the person 101.

For each of the embodiments of the computing device 106, the computing device 106 may include various types of logic circuitry, including, but not limited to, microprocessors, controllers, digital signal processors (DSPs), application specific integrated circuits (ASICs), field-programmable gate arrays (FPGAs), central processing units (CPU), graphics processing units (GPU), programmable logic devices, memory (e.g., random access memory, volatile memory, non-volatile memory, etc.), or other discrete or integrated logic circuitry, as well as combinations of such components. The term "processing circuitry" may generally refer to any of the foregoing logic circuitry, alone or in combination with other logic circuitry, or any other circuitry for performing computations.

Aspects of the delivery device 102, the monitoring device 104, and the computing device 106 have been described above. One or more of the devices 102-106 may include a user interface (not shown) that presents information to the person 101 and/or receives information from the person 101. The user interface may include a graphical user interface (GUI), a display device, a keyboard, a touchscreen, a speaker, a microphone, a vibration motor, buttons, switches, and/or other types of user interfaces. Persons skilled in the art will recognize various types of user interfaces that may be used, and all such user interfaces are contemplated to be within the scope of the present disclosure. For example, where the computing device 106 is a consumer device such as a smart phone, tablet computer, laptop computer, or the like, the user interfaces would include a display device, a physical and/or virtual keyboard, and/or audio speakers provided by such consumer devices, among other things. In various embodiments, a user interface may notify the person 101 of sensed data (e.g., glucose level) and/or insulin delivery data (e.g., rates of historic, current, or future insulin delivery) and may present alerts to the person 101. In various embodiments, a user interface may receive inputs from the person 101, which may include, for example, a requested change in insulin delivery and/or a meal indication, among other things. The descriptions and embodiments above regarding user interfaces are exemplary, and other types and other uses of user interfaces are contemplated to be within the scope of the present disclosure.

The following describes communications between the devices 102-106 and cooperation between the devices 102-106 with respect to insulin delivery. As illustrated in FIG. 1, and as mentioned above, the devices 102-106 may communicate with each other via communication links 112-116. In various embodiments, the computing device 106 may control operation of the delivery device 102 and/or the monitoring device 104. For example, the computing device 106 may generate one or more signals (e.g., a command signal) that cause the delivery device 102 to deliver insulin to the person 101, e.g., as a basal dosage and/or a bolus dosage. In various embodiments, the computing device 106 may receive data associated with insulin delivery (e.g., insulin delivery data) from the delivery device 102 and/or receive sensed data (e.g., glucose levels) from the monitoring device 104 and may perform computations based on the insulin delivery data, the sensed data, and/or other data to control the delivery device 102. Insulin delivery data may include, but is not limited to, a type of insulin being delivered, historical insulin delivery rates and/or amounts, current insulin delivery rate and/or amount, and/or user input affecting insulin delivery. As persons skilled in the art will understand, in a closed-loop operating mode, computing device 106 may communicate dosage commands to the delivery device 102 based on a difference between a current glucose level in the body of the person 101 (e.g., received from the monitoring device 104) and a target glucose level (e.g., determined by the computing device 106). The dosage commands may indicate an amount of insulin to be delivered and/or a rate of insulin delivery and may regulate the current glucose level toward the target glucose level. Examples of closed-loop operations for insulin infusion systems are described in U.S. Pat. Nos. 6,088,608, 6,119,028, 6,589,229, 6,740,072, 6,827,702, 7,323,142, and 7,402,153, and in United States Patent Application Publication Nos.: 2014/0066887 and 2014/0066889. The entire contents of each of the foregoing patents and publications are hereby incorporated by reference herein.

With continuing reference to FIG. 1, the remote or cloud computing system 108 may be a proprietary remote/cloud computing system or a commercial cloud computing system including one or more server computing devices. The remote/cloud computing system 108 may provide additional computing resources on-demand as needed when the computing resources of a client computing device (e.g., the computing device 106) are not sufficient. The computing device 106 and the remote/cloud computing system 108 may communicate with each other through a communication link 118, which may traverse one or more communication networks (not shown). The communication networks may include, without limitation, an Ethernet network, Wi-Fi network, a cellular network, a satellite network, an intranet, an extranet, the Internet, and/or the Internet backbone, among other types of networks. Persons skilled in the art will recognize implementations for the remote/cloud computing system 108 and how to interface with such systems through various types of networks. For example, the remote/cloud computing system 108 may include an array of processing circuitry (defined above) and may execute machine-readable instructions. Such implementations, interfaces, and networks are contemplated to be within the scope of the present disclosure.

Accordingly, an exemplary therapy delivery system has been described above. For convenience, the description below may primarily refer to an insulin delivery system as an example of the therapy delivery system. However, it is intended that any aspect, embodiment, or description relating to an insulin delivery system shall be applicable to a therapy delivery system which delivers a therapy other than insulin.

Aspects of the present disclosure relate to event-oriented predictions of glycemic responses. The events may be specific to a person rather than to a population of people. In various embodiments, events may have various degrees of specificity. For example, meal events may include breakfast, lunch, dinner, snack, and/or beverage meal events, among other levels of specificity. Sleep events may include, for example, nap events and/and overnight sleep events, among others. Exercise events may include, for example, weight training, walking, jogging, and/or swimming exercise events, among others. An illness event may include, for example, fever, vomiting, and/or medication intake, among others. Such events are exemplary, and other events and/or other levels of specificity for events are contemplated to be within the scope of the present disclosure.

Figure 2:
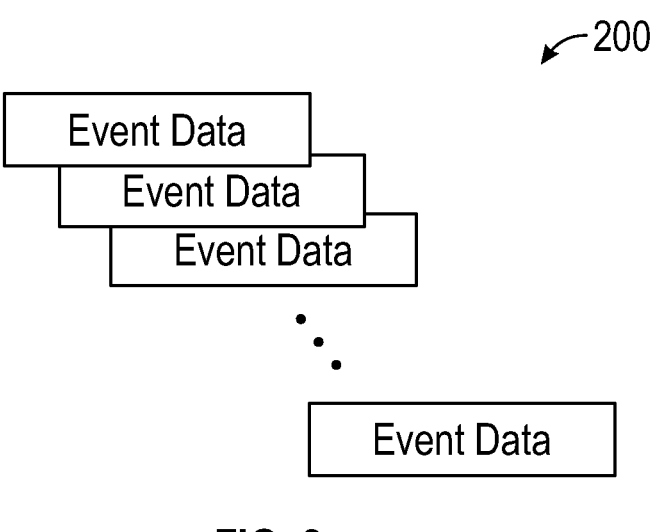
FIG. 2 is a diagram of an exemplary plurality of event data, in accordance with aspects of the present disclosure.

In accordance with aspects of the present disclosure, information related to an event may be stored as event data. Referring to FIG. 2, there is shown a plurality of event data 200 for a plurality of events. The plurality of event data 200 may be stored in a database, such as a relational database or a NoSQL database. The plurality of event data 200 may span any time period, such as several days to several months to several years, among other time periods, and may span different types of events, such as meal events, exercise events, sleep events, and/or illness events, among others. In various embodiments, the plurality of event data 200 may be stored by a computing device, such as computing device 106 of FIG. 1, and/or by a remote or cloud computing system, such as the remote or cloud computing system 108 of FIG. 1.

Figure 3:
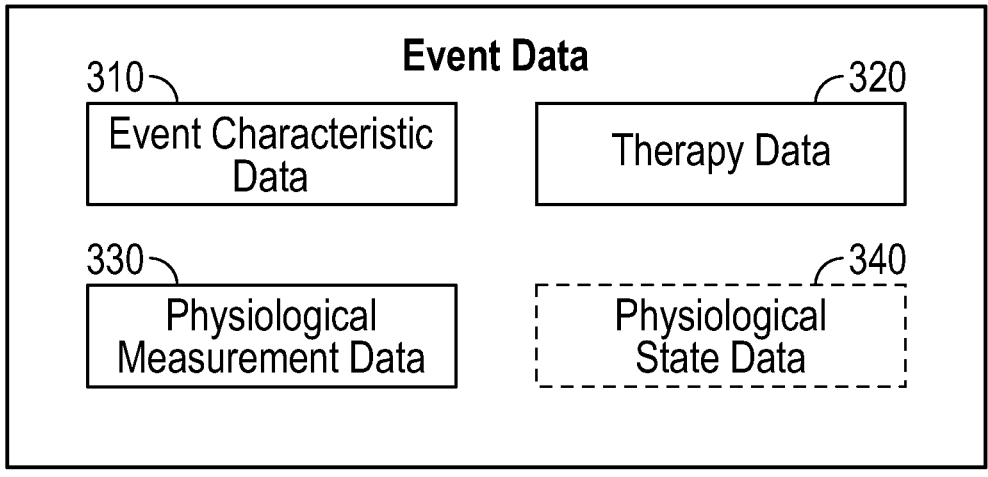
FIG. 3 is a diagram of exemplary content of event data, in accordance with aspects of the present disclosure.

FIG. 3 is a diagram of exemplary content of event data. The exemplary event data includes event characteristic data 310, therapy data 320, and physiological measurement data 330. Optionally, event data may include physiological state data 340. It should be appreciated that event data may include different content in various embodiments and that variations of FIG. 3 are contemplated to be within the scope of the present disclosure. For example, in some embodiments, therapy data 320 may be excluded from event data and/or additional data may be included in event data.

The event characteristic data 310 may include data corresponding to one or more variable characteristics that can be used to distinguish events. Non-limiting examples of event characteristic data 310 include meal content information (e.g., a carbohydrate content information for a meal), a meal type classification (e.g., breakfast, snack, etc.), an exercise activity classification (e.g., aerobic, anaerobic, jogging, swimming, etc.), activity level information (e.g., accelerometer data and/or heart rate data), and/or illness-related information (e.g., body temperature), among other things. Event characteristic data 310 may be obtained based on user input and/or data determined by a device. For example, computing device 106 may obtain a carbohydrate count provided via a user interface and/or automatically estimated based on time of day and similar meals.

The therapy data 320 may include data related to medicine delivery, such as by the delivery device 102 of FIG. 1. For example, the therapy data 320 may include the amount and timing of insulin actually delivered to the person by the delivery device in relation to an event (e.g., during the event).

The physiological measurement data 330 may include one or more measurements of a physiological characteristic. The physiological measurement data 330 may include, for example, a person's glucose level measurement obtained during an event from one or more monitoring devices (e.g., 104, FIG. 1).

The event characteristic data 310, the therapy data 320, and/or the physiological measurement data 330 for a person may be gathered and/or stored in association with an event (e.g., as event data for the person) in a variety of ways. In various embodiments, this may be achieved based on a manual indication by a user, such as by a user manually engaging a user interface of any of the devices 102-106 of FIG. 1 to indicate the beginning and/or the end of an event. In various embodiments, the event characteristic data 310, the therapy data 320, and/or the physiological measurement data 330 for a person may be automatically gathered and/or stored as event data without human intervention. For example, any of the devices 102-106, or some combination thereof, may automatically detect an event in progress and may gather and store the data 310-330 based on the automatic detection. Additionally or alternatively, one or more of the devices 102-106 may automatically gather and/or store any of the data 310-330 during post-processing of an event (e.g., processing after the occurrence of an event). For example, the data 310-330 of the devices 102-106 may be communicated to and stored by the remote or cloud computing system 108, which may process the data 310-330 to detect the beginning and end of events and may separate the data 310-330 according to corresponding events. Persons skilled in the art will recognize various techniques for automatically detecting certain events, such as using accelerometer data to determine various activities. Such and other techniques may also be used to process and separate data according to corresponding events. In various embodiments, some combination of manual indication and automatic processing may be used to gather and store event data in association with corresponding events. Such and other embodiments are contemplated to be within the scope of the present disclosure.

The physiological state data 340 may be representative of at least part of a person's physiological state during an event. For instance, a person's physiological model may include a set of equations having various parameters that can vary from person to person and from event to event. One or more of these parameters may be derived and stored as physiological state data 340 for an event. Non-limiting examples of physiological state data 340 include metabolic parameters corresponding to a rate of absorption of carbohydrates into the body (denoted as $m_1$) and a rate of converting carbohydrates into glucose (denoted as $k_m$). Notably, the parameters $m_1$ and $k_m$ for a particular person may have values that change over time (e.g., may fluctuate over the course of a single day).

It may be difficult to monitor a person's physiological state during an event, for example, based on direct measurement using sensors or other devices. Thus, the physiological state data 340 may be derived during event post-processing and included in event data. In various embodiments, the physiological state data 340 may be derived based on a physiological model that can be used to simulate the physiology and glycemic response of the person for whom the event characteristic data 310, therapy data 320, and physiological measurement data 330 were gathered. As will be described in greater detail in connection with FIG. 6, a person's physiological state may be derived using the physiological model as well as the event characteristic data 310, therapy data 320, and/or physiological measurement data 330.

FIG. 4 shows a flow diagram of exemplary techniques for glycemic response prediction. The techniques of FIG. 4 may be performed by a remote or cloud computing system (e.g., 108, FIG. 1). In various embodiments, if a different computing system (e.g., computing system 106 of FIG. 1) has sufficient computing resources, some or all of the techniques of FIG. 4 may be performed on such a computing system.

The following provides a summary of the blocks of FIG. 4. Blocks 410-430 relate to generation of a person-specific prediction model that correlates a person's glycemic responses to events with the person's physiological parameters during the events. Blocks 440-460 relate to application of the prediction model. Subsequent figures will describe the blocks in more detail.

At block 410, event data for a plurality of events of a person is accessed. The event data may be historical data for events that occurred in the past. In various embodiments, the accessed event data may be filtered for events of a particular type, such as event data for only meal events, only exercise events, only sleep events, or only illness events, among others. In various embodiments, the accessed event data may be filtered for a particular grouping of events, such as breakfast events, lunch events, dinner events, snack events, beverage events, nap events, overnight sleep events, jogging events, swimming events, fever events, or vomiting events, among others. The type or grouping of events may be specified by user input or may be automatically determined by one or more devices (e.g., 102-108, FIG. 1) to be the type or grouping for which a glycemic response prediction model is desired.

At block 420, similar events are identified for the person. As used herein, events are identified as being "similar" if their associated glycemic responses are similar (e.g., substantially identical). However, identifying similar events can be difficult due to variability in physiological state and/or variability in therapy provided in relation to events (e.g., the amount of insulin delivered in relation to a meal event may vary). Such variability can result in significantly different glycemic responses even for otherwise identical events occurring at different times of day. Thus, to facilitate identification of similar events, glycemic responses may be normalized for comparison (e.g., by using the same physiological state data and/or the same therapy data).

For example, Ronald may eat a cheeseburger for lunch and for dinner. Ronald's actual glycemic responses may be graphically represented as curves generated based on plotting glucose levels (e.g., stored as physiological measurement data 330) as a function of time. Despite the meal content being the same for both meals, the actual glycemic response curves for the meals may have significantly different shapes. This may be due to different metabolic rates at lunch versus dinner and/or different amounts of insulin delivered for lunch versus dinner. To account for such differences, Ronald's metabolic rates at lunch may be derived (e.g., using techniques that will be described in greater detail in connection with FIG. 6) and used to generate a hypothetical glycemic response curve for dinner (e.g., using techniques that will be described in greater detail in connection with FIG. 7) based on replacing Ronald's metabolic rates at dinner. Additionally or alternatively, the amount of insulin delivered for lunch may be used to generate a hypothetical glycemic response curve for dinner. Thus, if the actual glycemic response curve for lunch is similar to the hypothetical glycemic response curve for dinner, then the meals can be identified as being similar.

Comparing glycemic responses can be performed using a variety of techniques. In some embodiments, a person's physiological model may be used to simulate glycemic response curves for comparison. Additionally or alternatively, comparing glycemic responses may involve computing a mean absolute relative difference (MARD) for corresponding glucose levels at various points in time. Additionally or alternatively, comparing glycemic responses may involve computing the sum of the absolute values of differences between corresponding glucose levels at various points in time. Additionally or alternatively, comparing glycemic responses may involve applying a weighting function to the differences between corresponding glucose levels at various points in time. For example, a weighting function may penalize differences that exceed a predetermined threshold. Persons skilled in the art will recognize various techniques for comparing glycemic responses and/or for weighting differences between the glycemic responses, and all such techniques are contemplated to be within the scope of the present disclosure.

At block 430, a prediction model is developed based on the events determined to be similar events at block 420. As mentioned above, similar events result in similar glycemic responses if the variability among events is taken into consideration (e.g., by using the same physiological state data and/or therapy data to normalize glycemic responses). To build on this, similar events can be analyzed to determine how sources of variability (e.g., physiological state, therapy, and/or event characteristics) contribute to differences in glycemic responses. As will be explained in greater detail in connection with FIGS. 9 and 10, machine learning and/or statistical techniques may be used to develop a prediction model that accounts for the sources of variability. Such a prediction model enables greater accuracy in glycemic response predictions, because it is robust enough to account for variability among events.

A non-limiting example of such a prediction model is a set of one or more equations that can be used to predict a person's glycemic responses to meal events. The prediction model may take, as input, the person's metabolic rates $m_1$ and $k_m$ at the time of a meal, an estimated amount of carbohydrates included in the meal, and/or an amount of time elapsed since the start of the meal. The prediction model may provide, as output, information indicative of the person's glucose levels resulting from the meal (e.g., information indicating a cumulative total amount of glucose predicted to have appeared in the person's blood after the amount of time has elapsed since the start of the meal). This information may be used to generate a glycemic response curve representative of the person's glycemic response to a particular meal event (e.g., a curve representing the person's glucose levels as a function of time after the particular meal event has started).

As mentioned above, blocks 440-460 relate to application of the prediction model. At block 440, event data is obtained for a new event (e.g., an ongoing event being experienced by the person). The event data may include event characteristic data, therapy data, and/or physiological measurement data. For example, if the new event is a meal, the event data may include an estimated amount of carbohydrates in the meal, an amount of insulin delivered to the person, and/or a glucose level measured by a glucose sensor.

At block 450, physiological state data (e.g., 340, FIG. 3) may be determined or accessed for the person at the time of the new event. In the example context of a meal event, the physiological state data may include one or more metabolic rates (e.g., $m_1$, and $k_m$) that can fluctuate for a person throughout the day. The physiological state data may be determined (e.g., estimated) based on applying the person's physiological model to the event data obtained for the new event. For example, a person's physiological model may typically output estimated glucose levels based on input comprising event characteristic data and based on the person's physiological state data at the time of the event. Thus, the person's physiological state data may be back-calculated by providing physiological measurement data and event characteristic data as input to the person's physiological model.

In various embodiments, the physiological state data may be determined based on physiological state data for other events. For example, the values of rate $m_1$ and rate $k_m$ may be estimated based on the time of day and based on rate $m_1$ and rate $k_m$ for other events at such time of day. Additionally or alternatively, the values of rate $m_1$ and rate $k_m$ may be estimated based on the values of rate $m_1$ and rate $k_m$ for an immediately prior event. Other types of physiological parameters may be estimated in other ways, which persons skilled in the art will recognize.

At block 460, a glycemic response of the person to the new event is predicted based on application of the prediction model to the physiological state data determined or accessed at block 450. The physiological state data may be provided as input to the prediction model, which may output information indicative of the person's glycemic response to the new event. For example, if the new event is a meal, the prediction model may output values corresponding to cumulative total amounts of glucose predicted to have appeared in the person's blood after a particular amount of time has elapsed since the start of the meal. This information may be used to determine a point along a glycemic response curve and corresponding to the particular amount of time that has elapsed. Other points along the glycemic response curve can be determined using other prediction models (each model outputting a value for a different amount of time that has elapsed since the start of the meal). The prediction of a person's glycemic response to a new event will be further described in connection with FIG. 11.

The techniques of FIG. 4 are exemplary, and variations are contemplated to be within the scope of the present disclosure. For example, variations may exclude one or more blocks (e.g., blocks 410-430) and/or include one or more additional blocks (e.g., a block corresponding to determining, based on the predicted glycemic response, an amount of insulin to be delivered to the person).

Figure 5:
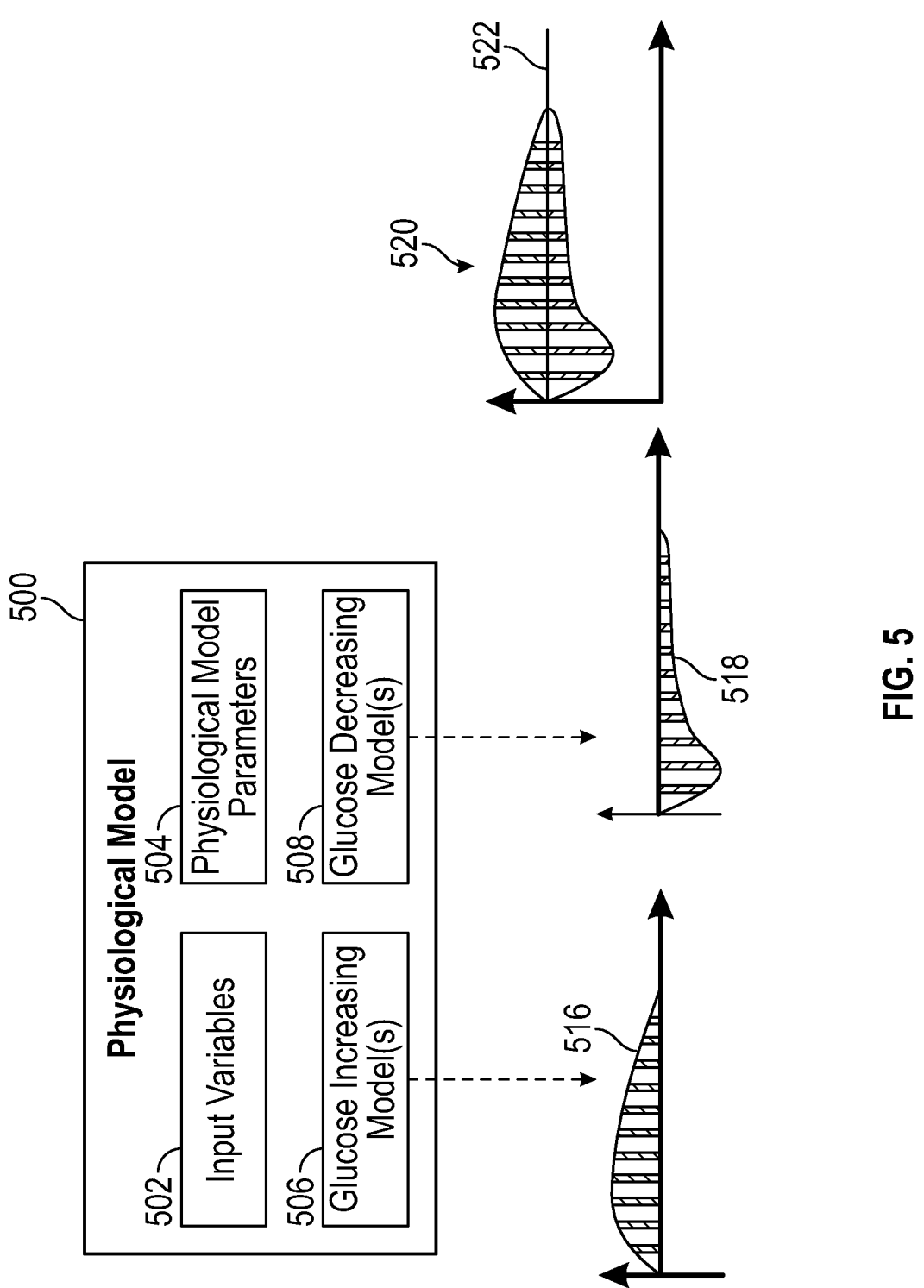
FIG. 5 is a diagram of an exemplary physiological model, in accordance with aspects of the present disclosure.

FIG. 5 shows a block diagram of an exemplary physiological model 500 for a person. As mentioned above, the physiological model 500 can be used to determine a person's physiological state at the time of an event (as will be further discussed in connection with FIG. 6) and/or to identify similar events (as will be further discussed in connection with FIG. 7). Instructions related to the physiological model 500 may be implemented in various programming languages and may execute on a remote or cloud computing system (e.g., 108, FIG. 1). In various embodiments, if a different computing system such as computing system 106 of FIG. 1 has sufficient computing resources, some or all instructions related to the physiological model 500 may be executed on such a computing system.

The physiological model 500 for a person includes input variables 502, physiological model parameters 504, one or more glucose increasing models 506, and one or more glucose decreasing models 508. The glucose increasing model(s) 506 may be one or more models which can be used to simulate mechanisms resulting in increased glucose levels in the person, such as meal consumption models and/or certain exercise models, among others. The glucose decreasing model(s) 508 may be one or more models which can be used to simulate mechanisms resulting in decreased glucose levels in the person, such as models for simulating insulin delivery to a body by a delivery device (e.g., 102, FIG. 1), among others. Various models can be used for simulating glucose increase and/or decrease in a person, and persons skilled in the art will recognize such models and how to implement them. The following may describe modeling and simulating glycemic response using a glucose increasing model and a glucose decreasing model, but it is intended that other types of models may be used for simulating glycemic response. For example, some models which can be used to simulate a glycemic response to a particular event (e.g., exercise) may account for both glucose increasing and glucose decreasing effects, and such models may be used in addition to and/or in place of the glucose increasing models and glucose decreasing models. The present disclosure relating to glucose increasing models and glucose decreasing models shall be applicable to such other models and embodiments, as well.

In accordance with aspects of the present disclosure, the glucose increasing model(s) 506 and the glucose decreasing model(s) 508 are configured to use input variables 502 and physiological model parameters 504. Input variables 502 may include event data (e.g., data 310-330) that can be used to simulate a glycemic response to an event. For example, for a meal event, the input variables 502 may include meal content information (e.g., a protein, fat, and/or carbohydrate count) and/or a beginning time for the meal. For an illness event, the input variables 502 may include body temperature and/or a beginning time for the fever, for example. For an exercise event, the input variables 502 may include a type of exercise, for example. Any of the events may include data indicating amounts and timing of insulin delivered to the person by, e.g., a delivery device (e.g., 102, FIG. 1). Other types of events and other types of input variables 502 are contemplated to be within the scope of the present disclosure.

The physiological model parameters 504 may be equation parameters reflecting a person's physiological state during an event and thus may differ from person to person and/or differ over time for a particular person. At least some of the physiological model parameters 504 may correspond to physiological state data 340 (FIG. 3) for an event. The physiological model parameters 504 may be used by the glucose increasing model(s) 506 and the glucose decreasing model(s) 508 to approximate the mechanisms of glucose increase or decrease in a person. For a meal event, for example, the physiological model parameters 504 may include a rate of absorption of carbohydrates into the body ($m_1$) and a rate of converting carbohydrates into glucose ($k_m$). Various physiological model parameters 504 may relate to how protein and fat affect the rate of carbohydrate absorption ($m_1$), among other things. For an exercise event, the physiological model parameters 504 may include a rate of endogenous glucose production attributable to physical exercise. For any of the events, the event data may include therapy data (e.g., 320, FIG. 3), which may include amount(s) and/or timing(s) of insulin delivered to the person (e.g., by a delivery device 102, FIG. 1). For insulin delivery, the physiological model parameters 504 may include a rate of insulin absorption in the body and insulin sensitivity factor, among other things. Various models can be used for simulating glucose increase and decrease in a person, and persons skilled in the art will recognize the physiological model parameters 504 for such models and how to implement them.

Using the input variables 502 and the physiological model parameters 504, the glucose increasing model(s) 506 can be used to simulate glucose increases over time 516 (e.g., the appearance of glucose in a person's blood). Using the input variables 502 and the physiological model parameters 504, the glucose decreasing model(s) 508 can be used to simulate glucose decreases over time 518 (e.g., glucose metabolism in the presence of insulin in a person's blood). The simulated glucose increases over time 516 and the simulated glucose decreases over time 518 may be combined and may be applied to a starting bodily glucose level 522 to provide the simulated bodily glucose levels over time 520 (e.g., a person's glycemic response to an event). Although FIG. 5 depicts the simulated bodily glucose levels over time 520 as the juxtaposition of the simulated glucose increases over time 516 and the simulated glucose decreases over time 518, it should be appreciated that the simulated bodily glucose levels over time 520 can be depicted as a single curve (e.g., 640, FIG. 6) resulting from subtracting the simulated glucose decreases over time 518 from the simulated glucose increases over time 516.

The illustration and description of FIG. 5 are exemplary. In various embodiments, a single model may be used to simulate multiple types of events (e.g., a combined sleep and illness model), or glycemic responses to a single type of event may be simulated using multiple models. In various embodiments, simulated bodily glucose levels over time 520 may be provided without separately modeling glucose increases and glucose decreases. Such and other variations are contemplated to be within the scope of the present disclosure.

Figure 6:
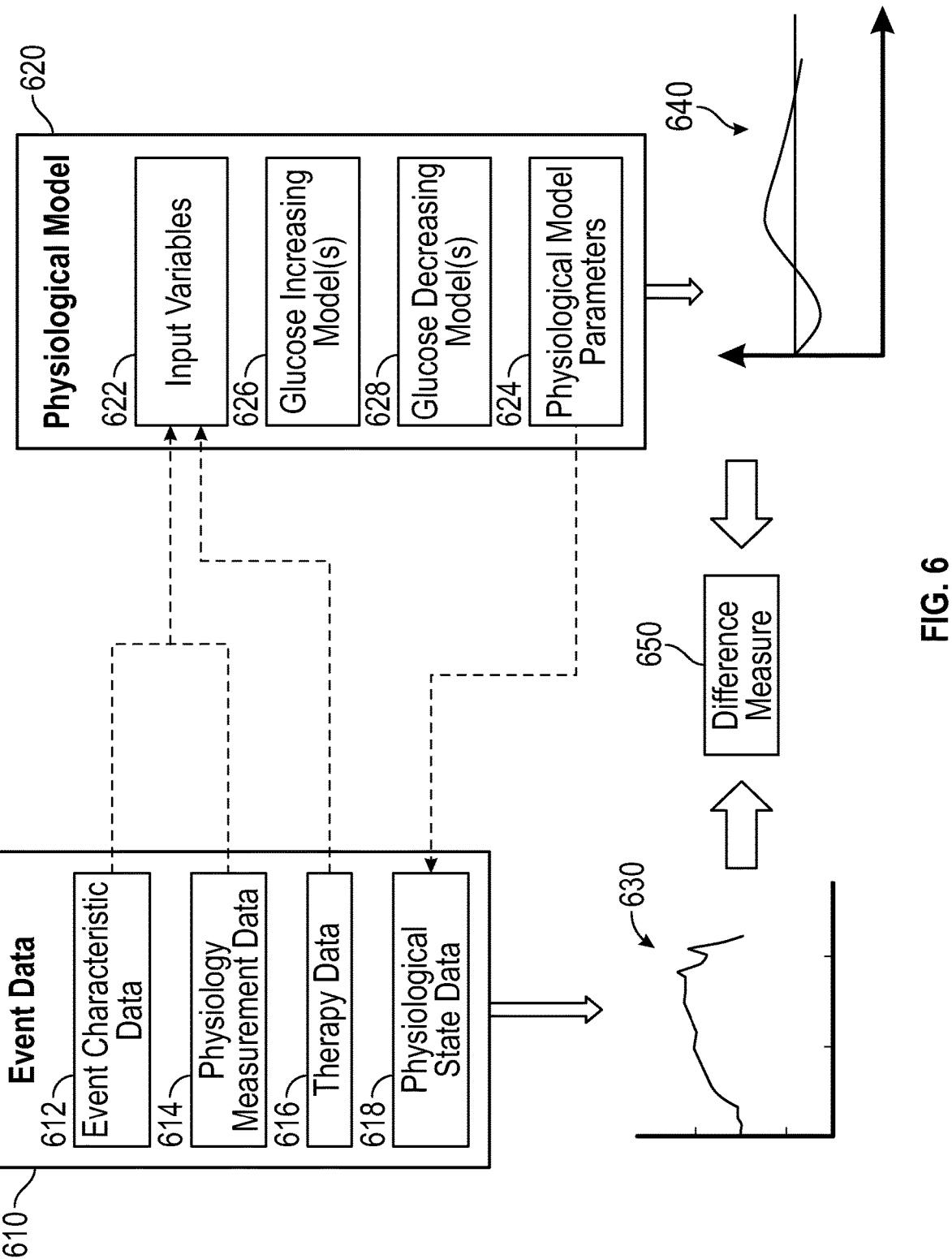
FIG. 6 is a diagram of exemplary techniques for determining a person's physiological state during an event, in accordance with aspects of the present disclosure.

Referring now to FIG. 6, there is shown a diagram of exemplary techniques for using a physiological model to determine physiological state data (e.g., the physiological model parameters which reflect at least part of the physiological state of a person) during an event. The techniques may be implemented in various programming languages and may execute on a remote or cloud computing system (e.g., 108, FIG. 1). In various embodiments, if a different computing system, such as computing system 106 of FIG. 1, has sufficient processing resources, some or all of the techniques may be executed on such a computing system.

Conceptually, a person's physiological state can be determined based on comparing actual glucose levels with simulated glucose levels. For example, at least part of an actual glycemic response 630 may be compared with at least part of a simulated glycemic response 640. The actual glucose levels may be obtained based on physiological measurement data 614 (e.g., one or more glucose levels measured by a glucose sensor), and the simulated glucose levels may be obtained based on a physiological model 620. Physiological model parameters 624 may be adjusted until the simulated glucose levels and the actual glucose levels match (e.g., have substantially similar values), at which point the physiological model parameters 624 should reflect the physiological state of the person for the event. Physiological state data 618 may be identified from the physiological model parameters 624 used to simulate glucose levels that match the actual glucose levels.

More specifically, at least some of the event data 610 (event characteristic data 612, physiological measurement data 614, and/or therapy data 616) may be provided to the physiological model 620 as input variables 622. The physiological model parameters 624 may initially be set to default values, values used for a previous event, or values roughly approximated based on the event data 610. Based on the input variables 622 and the physiological model parameters 624, the glucose increasing model(s) 626 and the glucose decreasing model(s) 628 may be used to provide simulated glucose increases and decreases over time, which can be combined and applied to a starting bodily glucose level to provide a simulated glycemic response 640. The simulated glycemic response 640 can be compared with the actual glycemic response 630 of the person to determine a difference measure 650 between them, such as mean absolute relative difference (MARD) or another difference measure. The physiological model parameters 624 may be iteratively adjusted, subject to physiological constraints for the parameter values, to minimize the difference measure 650. The physiological model parameters 624 corresponding to the minimum difference measure 650 may be identified, and at least some of the physiological model parameters 624 may be stored as physiological state data 618 representative of the physiological state of the person during the event.

All or part of the glycemic responses 630 and 640 may be compared. For example, to determine a person's physiological state for a past event, the glycemic responses 630 and 640 may be compared in their entireties, whereas to determine a person's physiological state for an ongoing event, corresponding portions of the glycemic responses 630 and 640 may be compared.

Persons skilled in the art will recognize various ways of adjusting the physiological model parameters 624 to minimize the difference measure. Such and other techniques are contemplated to be within the scope of the present disclosure. The illustration and description of FIG. 6 are exemplary, and variations are contemplated to be within the scope of the present disclosure.

Figure 7:
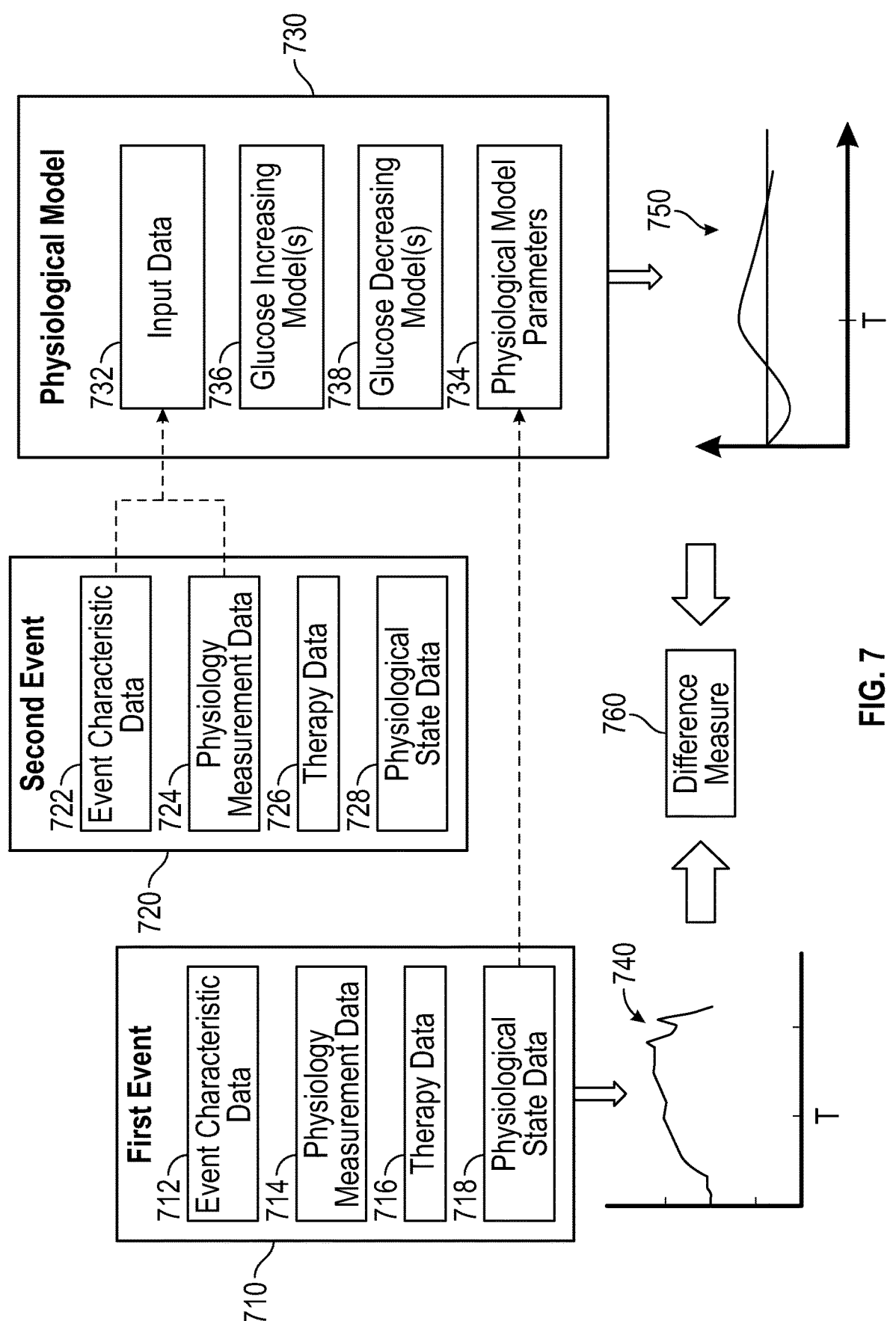
FIG. 7 is a diagram of exemplary techniques for identifying similar events, in accordance with aspects of the present disclosure.

FIG. 7 shows exemplary techniques for using a physiological model to identify similar events. The techniques depicted in FIG. 7 involve event data for a plurality of events including a first event 710 and a second event 720, each of which has associated event characteristic data (e.g., 712 and 722), physiological measurement data (e.g., 714 and 724), therapy data (e.g., 716 and 726), and/or physiological state data (e.g., 718 and 728). However, to identify similar events while accounting for variability among events, normalized glycemic responses may be compared. Normalization may involve using the same physiological state data and/or the same therapy data for each event of the plurality of events.

For example, FIG. 7 depicts normalization based on using the physiological state data 718 of the first event 710 for both the first event 710 and the second event 720. The techniques of FIG. 6 may be used to obtain the physiological state data 718 for the first event 710. In the example of FIG. 7, a physiological model 730 is used to simulate a glycemic response 750 to the second event 720 using at least the event characteristic data 722 and physiological measurement data 724 of the second event 720 while borrowing the physiological state data 718 of the first event 710.

The simulated glycemic response 750 to the second event 720 may be compared with an actual glycemic response 740 to the first event 710 (e.g., obtained based on physiological measurement data 714) to determine a difference measure 760, which may be indicative of a degree of similarity between glycemic responses. The difference measure 760 may be determined in a variety of ways. For example, the difference measure 760 may be a mean absolute relative difference (MARD) calculation for a pair of glycemic responses. Other techniques for determining difference measures are also contemplated. For example, the difference measure 760 may be the sum of the absolute value difference between the actual glycemic response 740 and the simulated glycemic response 750. In various embodiments, the difference measure 760 may be computed based on applying a weighting function to differences such that differences exceeding a predetermined threshold are penalized.

The difference measure 760 may be compared to a predetermined threshold to determine whether a pair of events are similar. For example, if the difference measure 760 is less than a predetermined threshold, the second event 720 may be identified as being similar to the first event 710. However, if the difference measure is greater than or equal to the predetermined threshold, the second event 720 may be identified as being dissimilar to the first event 710. Other techniques for determining similarity are contemplated to be within the scope of the present disclosure.

In various embodiments, the difference measure 760 may be computed for the glycemic responses 740 and 750 in their entireties. In various embodiments, the difference measure 760 may be computed for corresponding portions of the glycemic responses 740 and 750. For example, FIG. 7 depicts each of the glycemic responses 740 and 750 as including a portion from the start of the event to a time T, and these portions can be compared to compute the difference measure 760.

In accordance with aspects of the present disclosure, the techniques of FIG. 7 may be performed for more than two sets of event data (e.g., for every pair of event data depicted in FIG. 2). For example, if there are a number m of event data, the techniques of FIG. 7 may be performed for every pair of event data (each pair including an event data i and an event data j), where i and j are each in the range [1, m], and i≠j.

Figure 8:
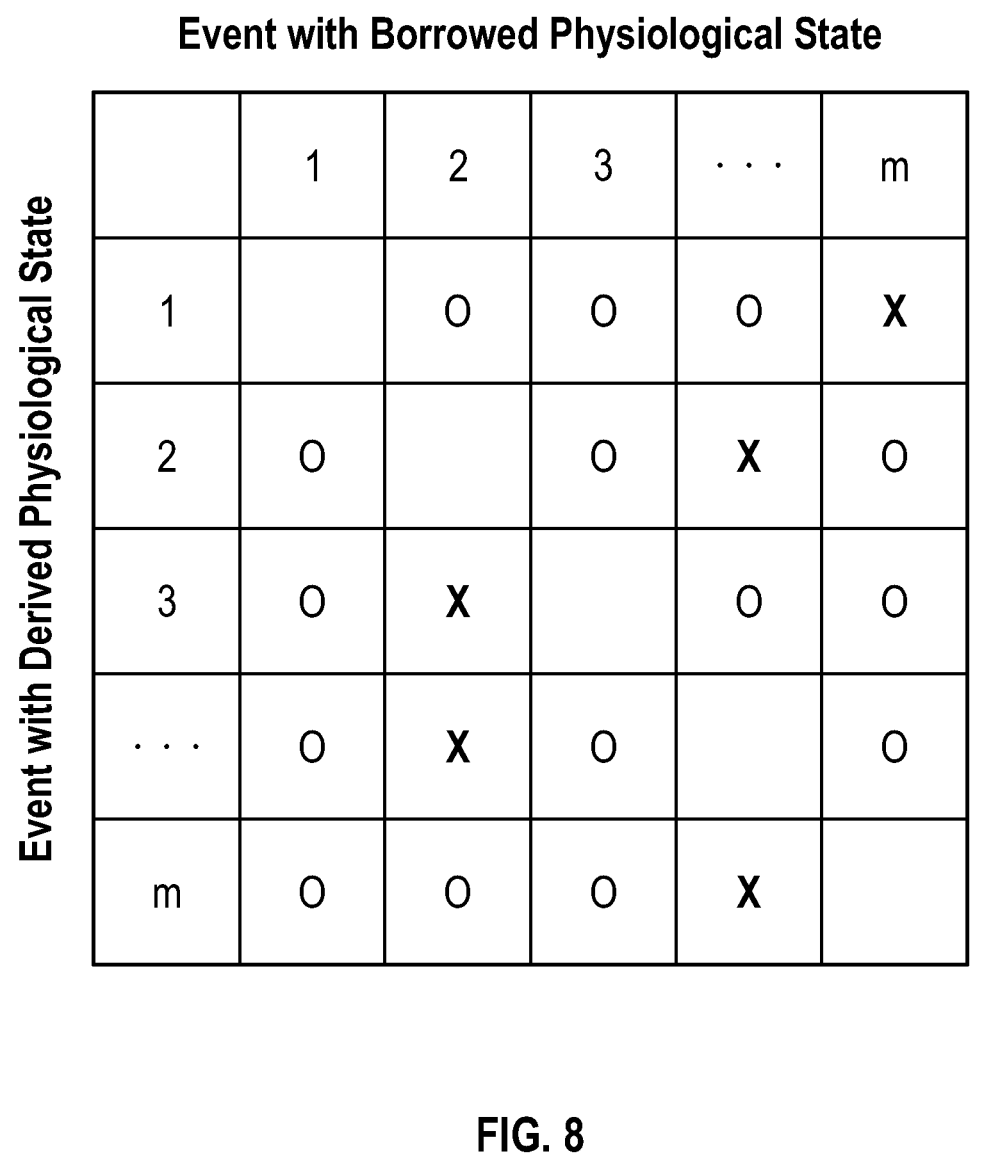

Event similarity determinations may be organized in a table, such as that shown in FIG. 8, where a circle indicates similar events and an "x" indicates dissimilar events. The table of FIG. 8 includes similarity determinations based on comparisons of glycemic responses over a particular time duration (e.g., a time duration from the start of an event to a time T). In accordance with aspects of the present disclosure, a separate table can be generated to include similarity determinations based on comparisons of glycemic responses over a different time duration (e.g., time duration from the start of an event to a different time T').

The table of FIG. 8 includes a plurality of rows. Each row may correspond to a similarity determination using different physiological state data. For example, the second row may correspond to a similarity determination using the physiological state data of Event 1, whereas the third row may correspond to a similarity determination using the physiological state data of Event 2.

Figure 9:
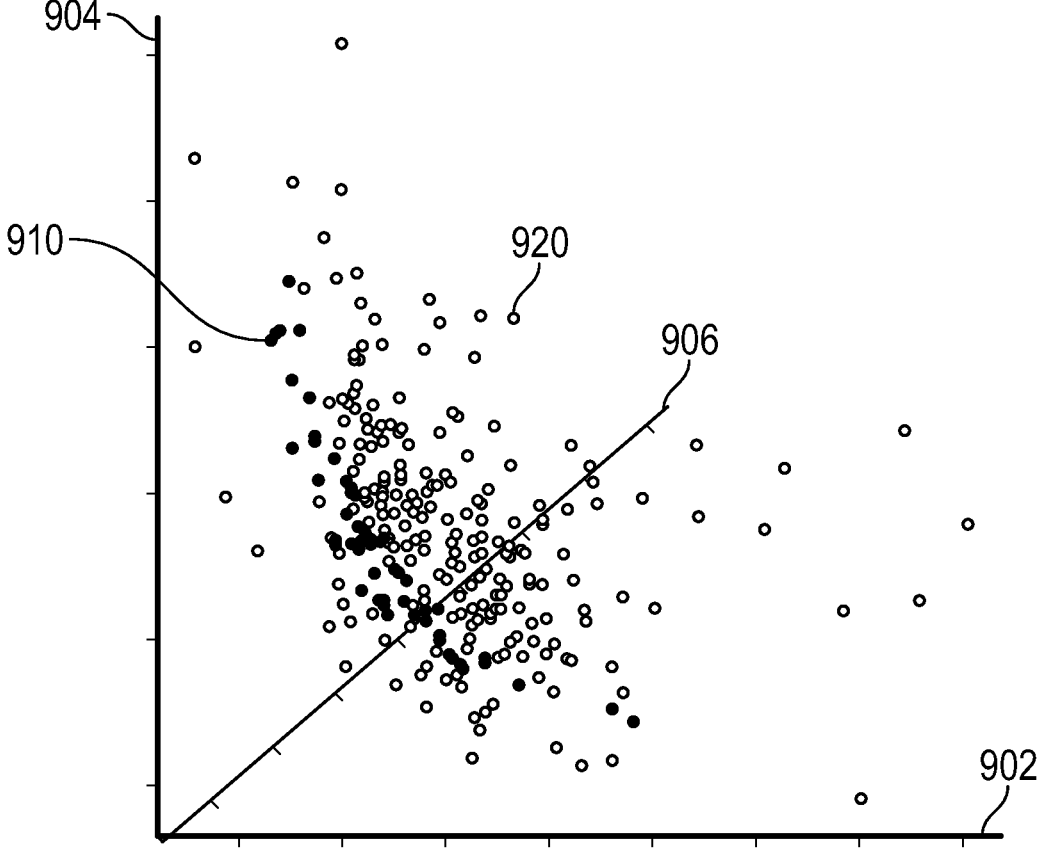
FIG. 9 is a graph showing an exemplary grouping of similar events, in accordance with aspects of the present disclosure.

As mentioned above, similar events can be analyzed to determine a prediction model useful for predicting glycemic responses based on physiological state data. The analysis may involve generating a graphical representation of the similar events using physiological state data for the similar events. FIG. 9 provides an example of such a graphical representation. Although FIG. 9 depicts a three-dimensional representation, it should be appreciated that the techniques described herein can be practiced with a graphical representation having a different number of dimensions (e.g., fewer than three dimensions or more than three dimensions).

Each axis 902-906 may correspond to a different input variable for the prediction model. However, at least one axis may correspond to a parameter included in physiological state data. For instance, using a meal event example, axis 902 may correspond to values of the parameter $k_m$ and axis 904 may correspond to values of the parameter $m_1$. Optional axis 906 may correspond to values of carbohydrate count. Events may be plotted according to their respective values of $m_1$, and/or carbohydrate count.

The graphical representation of FIG. 9 includes a grouping of events that have been identified as similar events 910 according to a single row of the table of FIG. 8. The grouping distinguishes the similar events 910 from dissimilar events 920. In accordance with aspects of the present disclosure, the similar events 910 may be used to determine a prediction model based on fitting a curve or surface to the similar events 910. For a graphical representation in two dimensions, a curve may be fitted to a group of similar events, and for a graphical representation in three dimensions, a surface may be fitted to a group of similar events. For generality, the term "hyper-surface" may be used herein to refer to a fit in n dimensions and thus can refer to a line, curve, or surface. Persons skilled in the art will understand various ways of fitting a hyper-surface to data, including automated programs and/or algorithms for performing such fitting.

For the sake of providing a clear example, the graphical representation of FIG. 9 includes only one grouping of similar events 910. However, it should be appreciated that in some embodiments, the graphical representation may include a plurality of groupings, and each grouping may correspond to a different row of the table of FIG. 8. Furthermore, a separate hyper-surface may be fitted to each grouping such that the graphical representation includes a plurality of hyper-surfaces. From the plurality of hyper-surfaces, a consensus hyper-surface may be determined, for example, using machine learning or statistical techniques.

In accordance with aspects of the present disclosure, the consensus hyper-surface may be reduced to one or more equations to be included in the prediction model. The one or more equations may relate an output variable to at least one of the input variables corresponding to an axis of the graphical representation. For instance, using a meal event example, the one or more equations may relate an output variable to $k_m$, $m_1$, and/or a carbohydrate count. The output variable may be indicative (e.g., predictive) of a person's glycemic response to an event (e.g., an ongoing event). For instance, using a meal event example, the output variable may indicate all or part of the area under a curve representative of a rate at which glucose is predicted to appear in a person's blood as a function of time.

As used herein, fAUC refers to a fractional area under a curve, and an output variable may correspond to a fAUC value when the output variable indicates a part of the area under a curve. Many types of fAUC values are referenced herein. For example, $fAUC_{Ra}$ refers to a part of the area under a curve representative of a rate at which glucose appears in a person's blood as a function of time, and $fAUC_{Ip}$ refers to part of the area under a curve representative of a rate at which insulin appears in a person's blood as a function of time. In some embodiments, the fAUC value may correspond to a fractional area under the curve between times $T_1$ and $T_2$. In such embodiments, $fAUC^{T1,T2}$ may refer to the fractional area. When $T_1$ corresponds to the start time of an event, $fAUC^{T1,T2}$ may simply be written as $fAUC^T$, where $T_2$ is simply written as T and can correspond to any point in time between the start and end of an event (e.g., T may correspond to a time that typically corresponds to the end of an event).

Notably, fAUC values can be used to predict future glucose levels in a person. For example, a $fAUC_{Ra}^T$ value may provide a cumulative total amount of glucose that is expected to appear in the person's blood from the start of an event to a time T, and a $fAUC_{Ip}^T$ value may provide a cumulative total amount of insulin that is expected to appear in the person's blood from the start of the event to the time T. Multiplying the $fAUC_{Ip}^T$ value by the person's insulin sensitivity factor would yield a cumulative total amount of glucose expected to be metabolized from the start of the event to the time T, and this cumulative total amount of glucose expected to be metabolized can be subtracted from the $fAUC_{Ra}^T$ value to yield the person's glucose level at time T (relative to the person's glucose level at the start of the event). Thus, the person's glucose level at time T may be obtained from the output of the prediction model.

The prediction model may be generated in various ways, including by using machine learning techniques and/or statistical analysis techniques (e.g., regression analysis), among other things. Persons skilled in the art will recognize such techniques and how to implement them.

Figure 10:
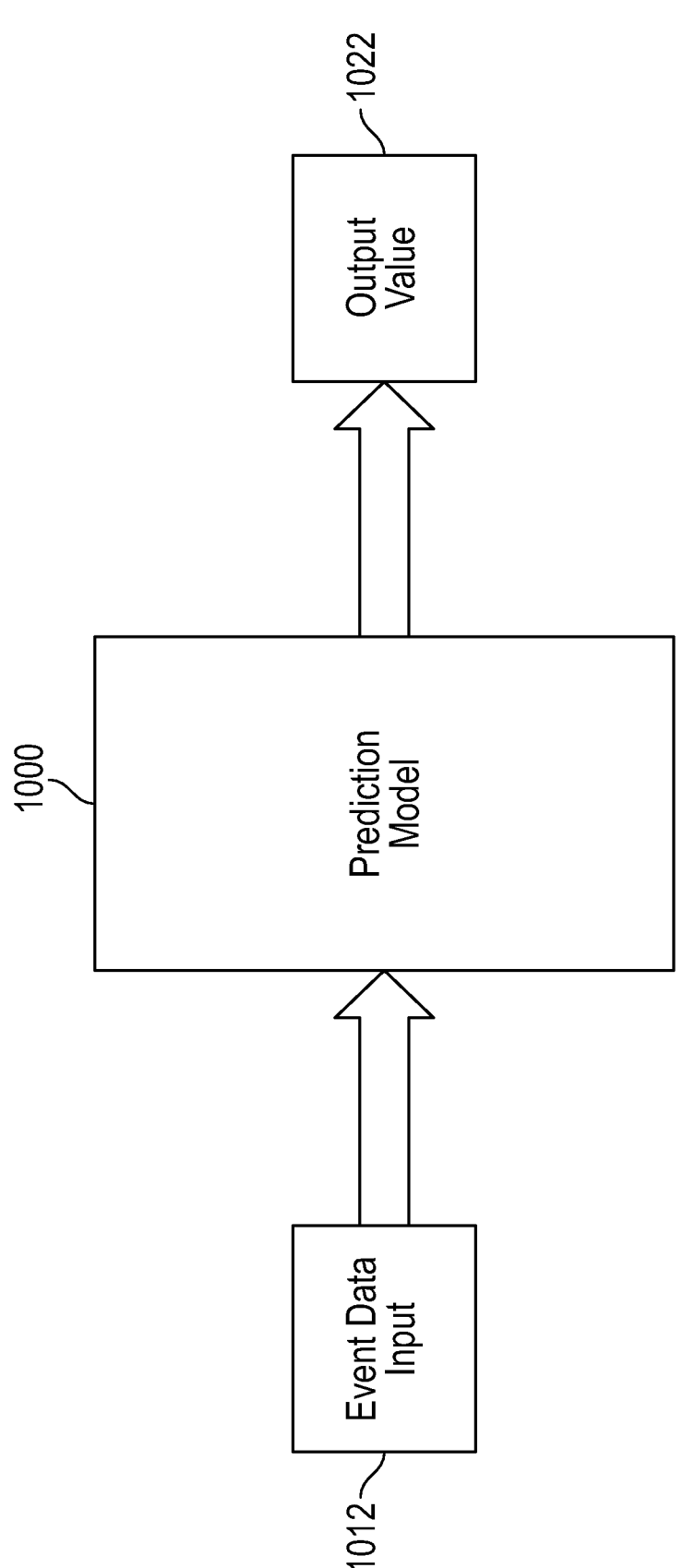
FIG. 10 is a diagram of an exemplary prediction model, in accordance with aspects of the present disclosure.

FIG. 10 shows an exemplary prediction model 1000. As mentioned above, the prediction model 1000 may be generated using an algorithm configured to fit one or more hyper-surfaces to one or more groupings of similar events (910, FIG. 9), to determine a consensus hyper-surface, and/or to reduce the consensus hyper-surface to one or more equations. In various embodiments, the prediction model 1000 may be determined based on performing at least part of the algorithm on a neural network. In various embodiments, at least part of the algorithm may be performed on a remote or cloud computing system (e.g., 108, FIG. 1). In various embodiments, if a different computing system (such as computing system 106 of FIG. 1) has sufficient computing resources, some or all aspects of the algorithm may be performed on such a computing system. Persons skilled in the art will understand various types of machine learning algorithms and how to implement them.

Event data input 1012 may be provided as input to the prediction model 1000. The event data input 1012 may include some or all of physiological state data (340, FIG. 3) and may optionally include event characteristic data (310, FIG. 3). For example, if the prediction model 1000 is developed for use in predicting glycemic responses to meal events, the event data input 1012 may include physiological parameters $k_m$ and $m_1$ and may optionally include an estimated total amount of carbohydrates consumed during the meal event.

Based on the event data input 1012 for an event, the prediction model 1000 yields an output value 1022 indicative of a glycemic response to the event (e.g., information indicating a cumulative total amount of glucose predicted to have appeared in the person's blood since the start of the event). The output value 1022 may be specific to a particular duration since the start of the event (e.g., a duration from the start of the event to a time T). Thus, different prediction models may be used to determine output values corresponding to different durations since the start of an event.

As mentioned above, the output value 1022 may be used to derive a glycemic response to the event. For example, the output value 1022 may be a $fAUC_{Ra}^{T}$ value that can be used to determine a glucose value along a glycemic response curve.

Figures 11A, 11B:
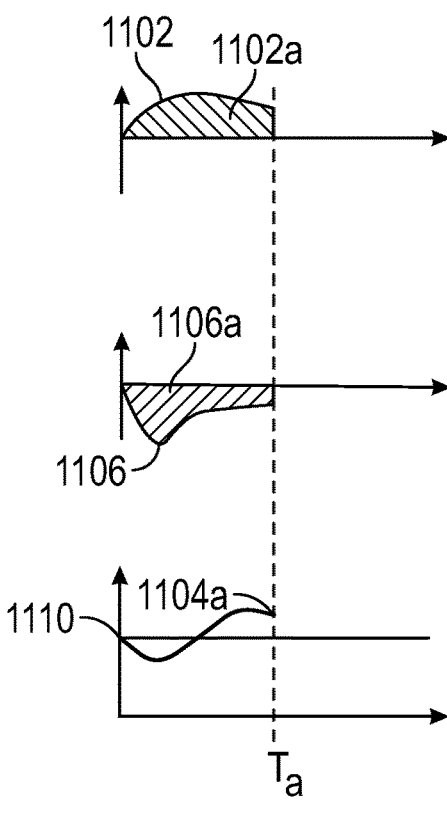
FIGS. 11A-B are diagrams of exemplary techniques for deriving a glycemic response curve based on output of a prediction model, in accordance with aspects of the present disclosure.

FIGS. 11A-B depict example techniques for deriving a glycemic response curve. The glycemic response curve can be derived based on physiological measurement data (e.g., 330, FIG. 3) and the output value 1022 of the prediction model 1000. For example, physiological measurement data may be used to determine point(s) near the beginning of the glycemic response curve, and the output value 1022 may be used to predict a point near the end of the glycemic response curve. As mentioned above, the output value 1022 may be specific to a particular duration since the start of an event. Thus, the output value 1022 may be used to determine a glucose value corresponding to a particular time value T after the start of an event. Accordingly, different prediction models may be used to obtain different output values that each correspond to different time values after the start of the event.

For example, FIGS. 11A-B depict a glycemic response curve generated based on two different output values obtained from two different prediction models. FIG. 11A depicts a portion of the glycemic response curve generated based on an output value specific to a duration from the start of an event to a time $T_a$, and FIG. 11B depicts a portion of the glycemic response curve generated based on an output value specific to a duration from the start of the event to a time $T_b$. Although two different time values are depicted in FIGS. 11A-B, it should be appreciated that the techniques disclosed herein can be practiced with any number of time values (e.g., more than two time values or less than two time values).

In FIGS. 11A-B, glucose values 1104a-b correspond to points along the glycemic response curve at time values $T_a$ and $T_b$, respectively. The glucose values 1104a-b may be determined based on subtracting fAUC values 1106a-b from fAUC values 1102a-b, respectively. For example, curve 1102 may be representative of a rate at which glucose appears in a person's blood as a function of time, and the fAUC value 1102a may correspond to a cumulative total amount of glucose expected to appear in a person's blood between the start of the event to the time value $T_a$; whereas curve 1106 may be representative of a rate at which glucose is metabolized in a person's blood as a function of time, and the fAUC value 1106a may correspond to a cumulative total amount of blood glucose that is expected to be metabolized between the start of the event to the time value $T_a$. Thus, subtracting the fAUC value 1106a from the fAUC value 1102a would yield a net change in glucose level (relative to the person's glucose level 1110 at the start of the event) expected to occur by the time value $T_a$.

As mentioned above, the fAUC values 1102a-b may be obtained from different prediction models. For example, a first prediction model may yield a first output value specific to a duration from the start of an event to a time value $T_a$, and a second prediction model may yield a second output specific to a duration from the start of the event to a time value $T_b$. In some embodiments, each prediction model may be generated at a remote or cloud computing system (e.g., one or more server computers) and communicated to a different computing system (e.g., a smartphone), where the prediction models are locally stored for application at the different computing system.

The fAUC values 1106a-b may be determined based on providing therapy data (e.g., 320, FIG. 3) to the physiological model 500 to simulate glucose metabolism. For example, the model 500 may provide an equation or a curve representative of a rate at which glucose is metabolized in the presence of insulin, and integrating the equation or curve through the time values $T_a$ and $T_b$ would respectively yield cumulative total amounts of glucose expected to be metabolized as of the time values $T_a$ and $T_b$.

For the avoidance of doubt, the techniques depicted in FIGS. 11A-B are merely provided as examples, and the glycemic response curve can be derived using other techniques. For example, some techniques may involve using the fAUC values 1102a-b to determine glucose values 1104a-b without accounting for glucose metabolism (e.g., in the absence of therapy data).

In some embodiments, the output value 1022 of the prediction model 1000 may be used for therapy determination. For example, the output value 1022 may be used to determine an insulin delivery amount (e.g., the size of a meal bolus to be delivered to a person in relation to a meal event) for maximizing time-in-range. In such embodiments, the predicted glycemic response would be a desired glycemic response. Thus, the glucose values 1104a-b and the fAUC values 1102a-b could be used to back-calculate the fAUC values 1106a-b, which could be used to determine the total amount of glucose that would be metabolized to achieve the desired glycemic response. For example, the fAUC values 1106a-b could be used to derive a glucose metabolism rate curve, and calculating the area under this curve would yield the total amount of glucose metabolized. To determine an insulin delivery amount, the total amount of glucose metabolized can be divided by an insulin sensitivity factor.

In some embodiments, therapy may be effected based on communicating a therapy determination toward a therapy delivery device. A non-limiting example of such a device is described below in connection with FIG. 12.

As mentioned above, therapy determinations may be communicated toward an insulin delivery device 1200 (e.g., from a cloud computing system 108 via an intermediary computing device 106 communicatively coupled to the device 1200). In such a device, insulin delivery may be performed based on internal communication between a central computing module (e.g., a microcontroller for device 1200 as a whole) and an insulin delivery module (e.g., including a microcontroller, a motor, and a pump). For instance, insulin delivery may be caused by the central computing module communicating a delivery command in the form of an electrical signal that travels via a communication fabric to the insulin delivery module. The central computing module may also be configured to communicate (e.g., via a transceiver) with a computing device (e.g., 106, FIG. 1) communicatively coupled to a remote or cloud computing system (e.g., 108, FIG. 1). The insulin delivery device 1200 may communicate various event data toward the remote or cloud computing system, which may communicate insulin delivery determinations toward the insulin delivery device 1200, in accordance with the techniques described herein.

Figure 12:
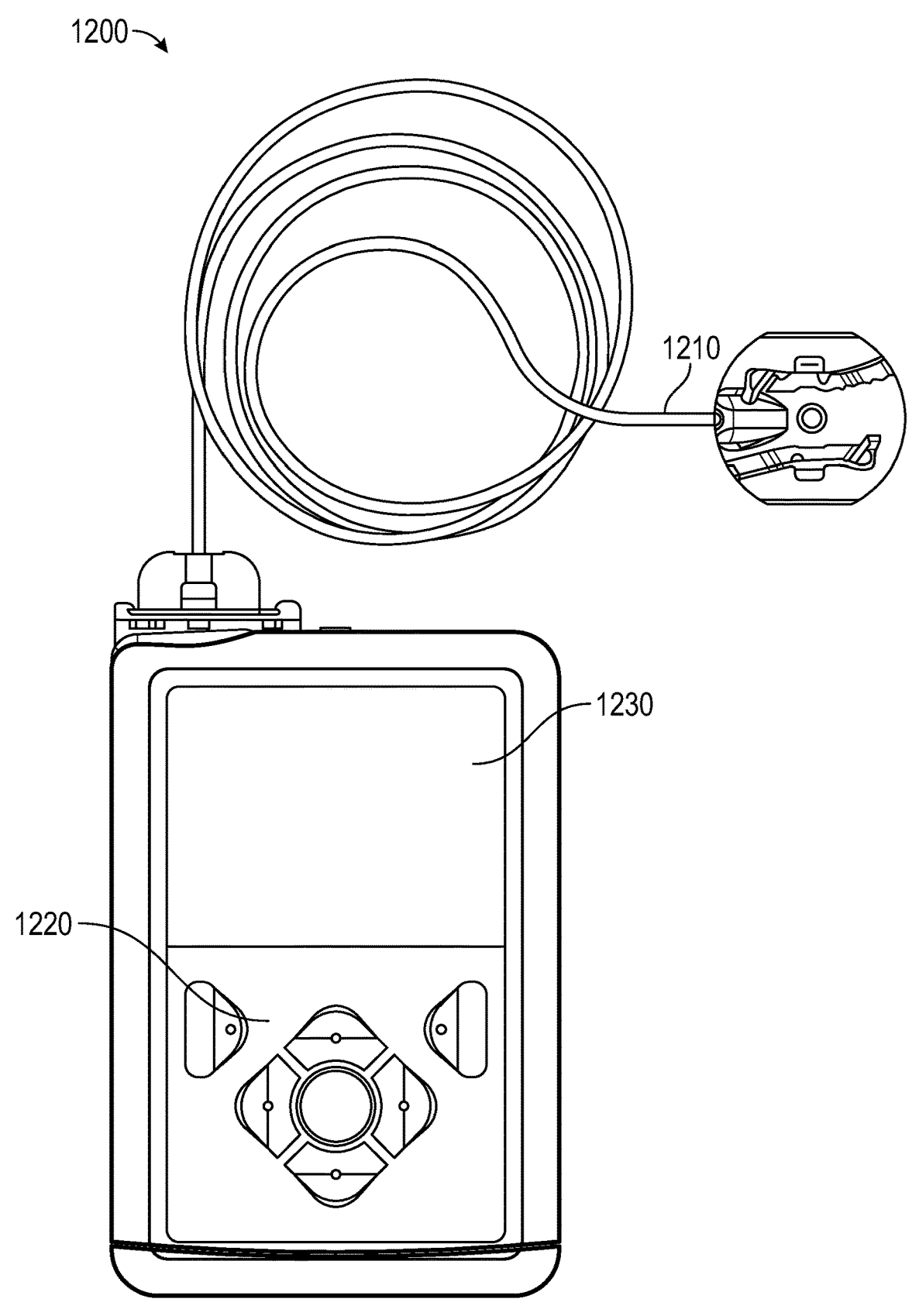
FIG. 12 is a diagram of an exemplary insulin delivery device, in accordance with aspects of the present disclosure.

The insulin delivery device 1200 can provide fast-acting insulin through a small tube 1210 configured for fluidic connection with a cannula inserted subcutaneously. The device 1200 can deliver two types of dosages—a basal dosage, which can be delivered periodically (e.g., every five minutes) in tiny amounts throughout the day and night, and a bolus dosage to cover an increase in blood glucose from meals and/or to correct high blood glucose levels. The illustrated insulin delivery device 1200 includes a user interface having button elements 1220 that can be manipulated to administer a bolus of insulin, to change therapy settings, to change user preferences, to select display features, and the like. The insulin delivery device 1200 also includes a display device 1230 that can be used to present various types of information or data to the user. In accordance with aspects of the present disclosure, a user of the insulin delivery device 1200 may use the button elements 1220 to input certain event data (e.g., event type, event start time, event details, etc.), and the user inputs can be confirmed using the display device 1230. The illustrated insulin delivery device 1200 of FIG. 12 is exemplary, and other types of insulin delivery devices and other techniques different from those described above are contemplated to be within the scope of the present disclosure.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to like elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described techniques, operations, methods, programs, algorithms, or codes may be converted to, or expressed in, a programming language or computer program embodied on a computer, processor, or machine-readable medium. The terms "programming language" and "computer program," as used herein, each include any language used to specify instructions to a computer or processor, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, Python, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. To the extent consistent, any or all of the aspects detailed herein may be used in conjunction with any or all of the other aspects detailed herein. Various alternatives and modifications can be devised by those skilled in the art without departing from the disclosure. Accordingly, the present disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system comprising:
one or more processors; and
one or more processor-readable media storing instructions which, when executed by the one or more processors, cause performance of:
accessing a prediction model correlating:
a person's glycemic responses to events, and
the person's physiological parameters during the events;
obtaining a glucose level measurement of the person during an event;
determining a physiological parameter of the person during the event based on applying a physiological model to the glucose level measurement, the physiological parameter being derived based on an iterative adjustment of one or more physiological model parameters to minimize a difference measure between at least one simulated glucose level generated by the physiological model and at least one actual glucose level based on the glucose level measurement;
predicting the person's glycemic response to the event based on applying the prediction model to the physiological parameter;
determining, based on the predicted glycemic response, an amount of insulin to deliver to the person; and
causing delivery of the amount of insulin by an insulin delivery device.

2. The system of claim 1, wherein the event is a meal event.

3. The system of claim 1, wherein the physiological parameter is a metabolic parameter.

4. The system of claim 3, wherein the metabolic parameter is a rate of absorption of carbohydrates into the person's body.

5. The system of claim 3, wherein the metabolic parameter is a rate of converting carbohydrates into glucose.

6. The system of claim 1, wherein the one or more processor-readable media further store instructions which, when executed by the one or more processors, cause performance of:
obtaining carbohydrate content information for the event.

7. The system of claim 1, wherein the one or more processor-readable media further store instructions which, when executed by the one or more processors, cause performance of:

obtaining insulin delivery information indicating an amount of insulin delivered to the person during the event.

8. The system of claim 7, wherein predicting the person's glycemic response comprises accounting for glucose metabolism caused by the amount of insulin delivered to the person during the event.

9. The system of claim 1, wherein communicating the amount of insulin toward the insulin delivery device comprises communicating the amount of insulin to an intermediary computing device that is communicatively coupled to the insulin delivery device.

10. The system of claim 1, wherein predicting the person's glycemic response comprises:

obtaining a value indicative of a cumulative total amount of glucose predicted to have appeared in the person's blood after a particular amount of time has elapsed since a start time for the event; and generating, based on the value, a curve representing the person's glucose levels during the particular amount of time.

11. The system of claim 10, wherein the value corresponds to a fractional area under a curve representative of a rate at which glucose appears in the person's blood as a function of time.

12. The system of claim 1, wherein the prediction model is configured to output a value corresponding to a cumulative total amount of glucose predicted to have appeared in the person's blood after a particular amount of time has elapsed since a start time for the event.

13. The system of claim 1, wherein the prediction model is generated based on a set of past events identified as eliciting similar glycemic responses from the person if the person's physiological parameters are identical during each past event of the set of past events.

14. The system of claim 13, wherein the set of past events includes a first event and a second event, the person's actual glycemic response to the first event being identified as similar to the person's hypothetical glycemic response to the second event, the hypothetical glycemic response to the second event being determined based on applying the person's physiological model to the person's physiological parameters during the first event.

15. The system of claim 13, wherein one or more of the person's physiological parameters during each past event, of the set of past events, are used to generate a graphical representation, and wherein a hyper-surface is fitted to the graphical representation to generate the prediction model.

16. The system of claim 1, wherein the prediction model is specific to the person.

17. The system of claim 1, wherein the physiological model comprises a glucose increasing model configured to simulate an increase in glucose levels of the person over time and a glucose decreasing model configured to simulate a decrease in glucose levels of the person over time, and wherein the at least one simulated glucose level is generated based on combining the simulated glucose increase from the glucose increasing model and the simulated glucose decrease from the glucose decreasing model applied to a starting bodily glucose level of the person.

18. The system of claim 1, wherein the iterative adjustment of the one or more physiological model parameters is subject to physiological constraints for values of the one or more physiological model parameters.

19. A processor-implemented method comprising:

accessing a prediction model correlating:

a person's glycemic responses to events, and the person's physiological parameters during the events;

obtaining a glucose level measurement of the person during an event;

determining a physiological parameter of the person during the event based on applying a physiological model to the glucose level measurement, the physiological parameter being derived based on an iterative adjustment of one or more physiological model parameters to minimize a difference measure between at least one simulated glucose level generated by the physiological model and at least one actual glucose level based on the glucose level measurement;

predicting the person's glycemic response to the event based on applying the prediction model to the physiological parameter;

determining, based on the predicted glycemic response, an amount of insulin to deliver to the person; and causing delivery of the amount of insulin by an insulin delivery device.

20. One or more non-transitory processor-readable media storing instructions which, when executed by one or more processors, cause performance of:

accessing a prediction model correlating:

a person's glycemic responses to events, and the person's physiological parameters during the events;

obtaining a glucose level measurement of the person during an event;

determining a physiological parameter of the person during the event based on applying a physiological model to the glucose level measurement, the physiological parameter being derived based on an iterative adjustment of one or more physiological model parameters to minimize a difference measure between at least one simulated glucose level generated by the physiological model and at least one actual glucose level based on the glucose level measurement;

predicting the person's glycemic response to the event based on applying the prediction model to the physiological parameter;

determining, based on the predicted glycemic response, an amount of insulin to deliver to the person; and causing delivery of the amount of insulin by an insulin delivery device.

\* \* \* \* \*